United States Patent [19]

Walton

[11] Patent Number: 4,886,843

[45] Date of Patent: Dec. 12, 1989

[54] DUAL-CURE CEMENT

[75] Inventor: Ian G. Walton, Congleton, United Kingdom

[73] Assignee: Imperial Chemical Industries Plc, London, England

[21] Appl. No.: 147,866

[22] Filed: Jan. 25, 1988

[30] Foreign Application Priority Data

Feb. 6, 1987 [GB] United Kingdom ................ 8702716

[51] Int. Cl.$^4$ ........................ C08F 2/50; C08G 79/00; C08J 3/28
[52] U.S. Cl. .................................. 522/174; 433/224; 522/28; 522/81; 522/96; 522/173; 522/181; 522/183; 523/116; 524/779; 526/304; 526/313; 528/205
[58] Field of Search ......................................... 526/313

[56] References Cited

U.S. PATENT DOCUMENTS

| | | | |
|---|---|---|---|
| 2,961,426 | 11/1960 | Engelhardt | 526/313 |
| 3,113,907 | 12/1963 | Tocker | 526/313 |
| 3,133,042 | 5/1964 | Tocker | 526/313 |
| 3,141,903 | 7/1964 | Fertig | 526/313 |
| 3,167,583 | 1/1965 | Goldberg | 526/313 |
| 3,635,889 | 1/1972 | Bowen | 526/313 |
| 4,813,876 | 3/1989 | Wang | 522/96 |

FOREIGN PATENT DOCUMENTS 0189903 8/1986 European Pat. Off. .
2041954 9/1980 United Kingdom .
2094326 9/1982 United Kingdom .

OTHER PUBLICATIONS

"Pulp Capping ...", Stanley et al; Operative Dentistry, Autumn 1985, vol. 10, No. 4, pp. 156–163.
French Search Report, Application No. 8801383.
Belgium Search Report, Application No. 8800023.
Prosser et al., "An Infra-Red Spectroscopic Study of the Setting Reactions of a Calcium Hydroxide Dental Cement". Journal of Materials Science, 14 (1979), pp. 2894–2900.

Primary Examiner—Lewis T. Jacobs
Assistant Examiner—Arthur H. Koeckert
Attorney, Agent, or Firm—Cushman, Darby & Cushman

[57] ABSTRACT

The compositions of this invention posses both calcium hydroxide cement characteristics and light cure characteristics and hence strong bonds are likely to form with both the tooth and conventional filling materials. There is less likelihood that a filling may fall out of a cavity.

The present invention provides a two component composition which comprises a first component comprising an ethylenically polymerizable compound which contains both a salicylate group and at least one acrylate, alkacrylate, acrylamide or alkacrylamide group and second component comprising calcium hydroxide or a suitable precursor to calcium hydroxide.

8 Claims, No Drawings

DUAL-CURE CEMENT

This invention relates to a composition that may be used in dental treatment. More particularly, this invention relates to a photopolymerizable calcium hydroxide cement.

As is well known, a healthy tooth has a pulp within the inner part of the tooth. Often, the pulp is exposed or nearly exposed if the tooth has a cavity or is in need of surgery. It is known that the pulp of a tooth is particularly sensitive to heat and pressure because it is associated with the nerve ending of the tooth. Therefore it has been the practice to protect the pulp during the filling of cavities and other dental procedures. In common practice, this may be achieved by for example lining the base of the tooth cavity with a cement-like lining. Commonly, the materials of the cement lining consist essentially of two components, one containing predominantly calcium hydroxide (or a precursor to calcium hydroxide, such as calcium oxide), and the other component containing predominantly a salicylate.

The setting of the cement like lining is generally believed to be through chelation of the calcium ions to form an ionic lattice structure with the salicylate. As the composition is water soluble, leaching of the calcium and hydroxide ions occurs, which has well known advantageous properties. The hydroxide ions help to create an alkaline environment, and as a result, are effective in killing bacteria. The calcium ions may help the regrowth of the tooth, by mitiating a remineralisation process.

In U.S. Pat. No. 3,047,408, a dental cement composition is described in which a stoichiometric excess of calcium hydroxide in a first paste is mixed with a second paste which contains an ester of a polyhydric alcohol and a salicylic acid or its esters.

The components are said to react to form a rigid and permeable mass of calcium phenolate with the calcium hydroxide being disposed therein.

Although, the types of two pack cement like systems described above have been useful in providing protection for the tooth pulp, such systems do have particular deficiencies. For instance, there is a relatively long setting time for the cement. A user must mix the two components (such mixing may be imperfect), place the mixture into position and wait for the setting reaction to occur. It could be said that there is a lack of 'command setting' ability in these type of compositions because the cement forming reaction begins as soon as the components are mixed. The user loses control over the setting time of the cement and must then work uninterrupted.

The mechanical properties of the ionic lattice structure cement are also relatively low. Given the impact that the user may exert upon a tooth, during operations, particularly when pushing a filling into place, a cement lining essentially needs to be of high strength.

Also, due to the ionic nature of the structure, the compositions are fairly soluble in water. In time, this may lead to some deterioration of the cement lining.

Although it is known that the ionic lattice structure cement binds well with the tooth, they do not form a strong bond with conventional filling materials such as amalgam or composites, and may work loose.

The addition of aluminium oxide as described in British Patent specifications 2173184A and 2173207A may improve the mechanical strength of the cement, the strength may be limited because of the nature of the ionic lattice.

A visible light-cure lining composition is associated with several advantages over the previous calcium hydroxide cured cements described hereinbefore. For example, the user has greater control over the setting of the composition because the setting reaction is initiated only by visible light. Typically the light source is in the visible wavelength range of from about 400 m$\mu$ to 600 m$\mu$. Wavelengths in the ultraviolet range have also been used. Such compositions generally contain a (meth)acrylate group. In the presence of a photosensitive catalyst, it is known that (meth)acrylate groups can polymerise so as to form a polymer of greater strength as a result of the formation of covalent bonds.

In European patent application 189903, there is described a light cured polymerisable composition, having low toxicity, for use in direct contact with living pulpal tissue such as bone and dentin. The composition includes at least one polymerisable monomer which polymerises by a free radical mechanism rather than by chelation or saponfication. The composition may include calcium hydroxide, but its presence is not an essential feature. A product falling within the scope of the above European patent application is a marketed as "Prisma VLC" and is said to be a light-cured base/liner composition. However it appears that in this material there is no possibility of a true 'cement' forming reaction. The cured material appears to be a methacrylate functionalised resin merely filled with calcium hydoxide. The calcium hydroxide present is used purely as a filler and does not take part in a cement forming reaction. The resin used in "Prisma VLC" composition is believed to be trimethylhexamethylenediisocyanate capped with hydroxypropylmethacrylate.

The advantages gained by the light-curing composition are offset by several disadvantages. For example the decreased solubility of the composition limits leaching of calcium ions from within the compositions may result in reduction of antibacterial and remineralisation capabilities of the cement. Because of the comparatively rapid cure of the lining composition, and the higher level of energy evolved in the formation of covalent bonds, the amount of heat produced in the reaction is significantly greater than that produced during an ionic (cement forming) curing reaction. This is a disadvantage in that the cement is generally used in the region of sensitive tooth pulp. The light curing lining compositions are also known to bond well with conventional filling materials but do not form a strong bond with the actual tooth.

According to the present invention an improved cement composition is provided which incorporates visible light and cement formation to provide a cured material with greater strength than a conventional two-pack cement.

The compositions of this invention possess both calcium hydroxide cement characteristics and light cure characteristics and hence strong bonds are likely to form with both the tooth and conventional filling materials. There is less likelihood that a filling may fall out of a cavity.

The present invention provides a two component composition which comprises a first component comprising an ethylenically polymerisable compound which contains both a salicylate group and at least one acrylate, alkacrylate, acrylamide or alkacrylamide group and second component comprising calcium hydroxide or a suitable precursor to calcium hydroxide.

In a further aspect of the present invention a method is provided for the production of an ethylenically polymerisable compound which contains both a salicylate group and at least one acrylate, alkacylate, acylamide or alkacylamide group. These compounds, hereinafter referred to as acrylosalicylates may be made in a two stage synthesis.

In the first stage salicylic acid or alkyl salicylate (where alkyl contains 1 to 8 carbon atoms, preferably 1 to 4) is condensed or transesterified respectively with a polyhydric alcohol, preferably containing at least three hydroxy groups in molar ratio 0.1:1 to m:1, preferably 0.3:1 to 3:1, most preferably, about 1.5:1, severally in the presence of a catalyst where m is the number of hydroxyl groups in the polyhydric alcohol. Depending on the molar ratio used, the resulting hydroxyalkyl salicylate will contain a range of pendant alkyl hydroxy groups.

Suitable polyhydric alcohols preferably contain three or more hydroxyl groups. Diols may also be used and are within the scope of the invention, but the properties of the cured cement composition may be less desirable.

Examples of suitable diols include:

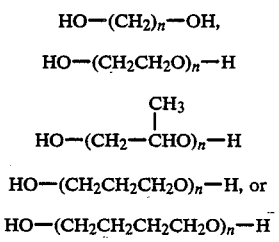

wherein n is an integer having a value of 1 to 10 inclusive

Examples of suitable triols include: Glycerol, triethanolamine, trimethylolpropane and the oxypropylated or oxyethylated derivatives of these compounds, the oxypropylated or oxyethylated derivatives of diethanolamine and monoethanolamine.

Examples of suitable tetrols include pentaerythritol and the oxypropylated or oxyethylated derivatives of pentaerythritol or tolylene diamine.

Examples of suitable hexitols include sorbitol and dipentaerythritol and the oxypropylated or oxyethylated derivatives of these compounds.

Examples of suitable octols include tripentaerythritol and the oxypropylated or oxyethylated derivatives of tripentaerythritol or sucrose.

Mixtures of polyhydric alcohols are also comprehended within the scope of the invention.

Examples of suitable salicylates include any compound having the structure

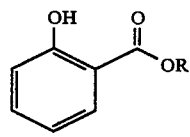

wherein R is H or $C_{1-8}$ alkyl, preferabe $C_{1-8}$ alkyl. It is most preferable that R is methyl.

The catalyst for the reaction may preferably be chosen from organometallic compounds such as tetrabutyl titanate or di-butyl-tin-dilaurate, or amines such as di-n-butyl amine, or any other suitable catalyst, but most preferably are alkali metal or alkali earth metal alkoxides such as for example, sodium methoxide. These preferred type catalysts appear to be associated with reduced colour in the reaction.

The salicylate group reacts with the hydroxy groups of the polyhydric alcohol to produce a mixture of polyhydric alcohol salicylate compositions. It is preferred that the reaction take place at above about 130° C. at atmospheric pressure. The number of salicylate groups attached to the alcohol is dependant upon the ratio of the initial components used and upon the number of hydroxy groups in the polyhydric alcohol.

In the second stage, the acrylosalicylate is produced by reacting the hydroxyalkyl salicylate product of the above first stage with an (alk)acrylic acid a derivative thereof suitably a halide, preferably in solution using any suitable solvent such as for example methylene chloride. The (alk)acryloyl halide may be a $C_{1-4}$ alkacryloyl halide, preferably methacryloylchloride. It is also preferred that the reaction be carried out in the presence of a suitable acid acceptor, preferably an amine, such as pyridine.

The molar amount of the (alk)acryloyl halide used in the reaction of the second stage depends upon the molar ratio used in the first stage reaction between the polyhydric alcohol and salicylate. The amount of (alk)acryloyl halide used will be that amount sufficient to react with the residual alcohol hydroxy groups in the hydroxy alkyl salicylate. The number of (alk)acrylate groups therefore produced in the acrylosalicylate is dependent upon the ratio of the hydroxyalkyl salicylate to alkacroyloyl halide used because the methacroyloyl halide reacts with the remaining hydroxy groups of the alcohol. By controlling the ratio of the various components of the reaction, the nature of the cement can be adjusted to suit particular requirements. The higher the ratio of (alk)acrylate groups to salicylate groups, the faster the light-cure and the greater the strength.

The second component of the present composition contains calcium hydroxide or a precursor therefor. Because the calcium hydroxide generally comes in a finely powdered form, it is also preferred to include a liquid plasticiser. Some examples of the preferred types of plasticisers include, ethyl p-toluene sulphonamide, dialkyl phthalate or any other suitable plasticiser. This plasticiser may also be a further (meth)acrylate or (dimeth)acrylate which also, serves as an additional monomer.

The composition must also include a photosensitive catalyst which may be present in either one or both components. Suitable photosensitive catalysts are described in British Patent specification 1408265, German Offenlegungschrift 2251041 and European Patent application 150952. A preferred photosensitive catalyst that may be included comprises camphorquinone and dimethylaminoethylmethacylate.

It is preferable that each of the two components be in paste form for ease of mixing and convenience of storing. The acrylosalicylate is generally a mobile light yellow liquid and the calcium hydroxide is usually in a powder form. Various fillers or mixtures of fillers may be incorporated to adjust viscosity and for any other reason.

The fillers may, for example, be any form of silica including comminuted crystalline silicas, e.g. sand, but also colloidal forms such as pyrogenic, fumed or precipitated silica. Any suitable silicate glass such as, for example, barium, other suitable oxide or a filler such as alumina, titanium dioxide, calcium difluoride, or zinc oxide which impart a desired property such as radio-opacity, hardness and refractive index may be used. Salts such as barium sulphate, calcium tungstate, calcium phosphate, typically used in conventional two-pack cement materials, may also be included. Mixtures of any or all of the above can appear in either or both of the components of the dual-cure cement, depending upon the desired viscosity.

In order that the dental cement may be produced in which the filler adheres particularly well to the cured cement, it is preferred that the filler be treated with a coupling agent which is capable of reacting with both the filler used and the components of the cement. The coupling agent should have the effect of increasing the strength of the bond between the filler and the components of the cement.

Suitable coupling agents for use with glass include silanes, e.g. $\gamma$-methacryloxypropyltrimethoxysilone, $\gamma$-aminopropyltriethoxysilane and $\gamma$-glycidoxypropyltrimethoxysilane.

Both compounds of the two-pack system may also preferably contain any suitable dispersing agents, such as for example stearic acid and alkyl stearates in general, so as to help create a paste-like form.

Suitable (meth)acrylate or (dimeth)acrylate liquids may also be incorporated as copolymerisable ethylenically unsaturated monomers. Other suitable monomers, the polymers of which should be water insoluble, include vinyl monomers, e.g. vinyl esters such as n-hexyl, cyclohexyl and tetrahydrofurfuryl acrylates and methacrylates. The monomers should be non-toxic. Also included would be suitable polyfunctional vinyl monomers, that is, monomers containing two or more vinyl groups. Suitable monomers include, for example, glycol dimethacrylates, diallyl phthalate and trialkyl cyanurate.

The invention is illustrated with reference to the accompanying examples.

EXAMPLE 1

Preparation of hydroxylalkylsalicylate (Glycerol Salicylate)

A 500 ml round-bottomed flask was charged with glycerol (46.0 g; 0.5 moles), methyl salicylate (119.7 g, 0.788 moles) and sodium methoxide (0.82 g, 0.015 moles). The molar ratio of methyl salicylate to glycerol was 1.58:1. The flask was fitted with a stirrer, thermometer and a reflux condenser topped with a still-head and a distillation condenser. Water at 70° C. was pumped through the reflux condenser, and cold water through the distillation condenser. The contents of the flask were stirred, and the temperature raised to about 210° C. Methanol distilled over; the progress of the reaction was followed by monitoring the methyl salicylate level, using gas chromatography. When the level had fallen to 17% the flask was allowed to cool.

Preparation of acrylosalicylate (Methacrylated Glycerol Salicylate)

A portion (123.5 g) of the above reaction product was weighed into a round-bottomed flask, along with pyridine (57.8 g; 0.73 moles) and dry methylene chloride (250 ml). The solution was raised to reflux, and to it was added methacryloyl chloride (72.4 g; 0.69 moles) in dry methylene chloride (150 ml), over 45 minutes. The contents of the flask were stirred for a further 2 hours, and then left to stand overnight. The solution was filtered into a separating funnel, and washed three times with an equal volume of distilled water. The methylene chloride layer was then run into a beaker, an equal volume of distilled water added, the solution was stirred vigorously and acidified with concentrated hydrochloric acid. The methylene chloride layer was separated, 0.1 g. of 'Topanol' 0 added, and the methylene chloride layer was removed on a rotary evaporator. Yield, 130 g.

Methyl salicylate content 14% (by Gas Phase Chromatography). 'Topanol'-trade mark Imperial Chemical Industries PLC, London, England).

A. Light Cure

A sample of methacrylated glycerol salicylate above was mixed with 0.75% w/w camphorquinone and 0.5% w/w dimethyl amino ethyl methacrylate. The time to gelation when illuminated by a 1000 Wm$^{-2}$ lamp, wavelength substantially between 440–490 m$\mu$ was measured as 60 seconds, using an oscillating rheometer. Such an examination was carried out using the method described in British Standard 5199:1975 paragraph 6.4, provision having been made to allow visible light to be directed onto the mixture.

B. Cement Cure

A portion of the light cure mixture (A) above was mixed by hand with an equal weight of a component comprising 50% calcium hydroxide and 50% triethylene glycol dimethacrylate. The time to gelation was measured on the oscillating rheometer was 4 minutes without illumination.

C. Surface Hardness of Cured Material

A sample of the mixture of the two components described in (B) was placed between two glass slides 1 mm apart. The sample was illuminated for 1 minute with a 1000 Wm$^{-2}$ lamp with the wavelength of the light substantially between 440–490 m$\mu$ with samples 2 mm thick. The sample was then allowed to age for 1 week under ambient conditions. The surface hardness of the cement was determined using a Zwick 3212 hardness tester, and found to be 14 VHN. (VHN: Vickers Hardness Number).

D. Comparison with Conventional Two-Pack Cements

Cure times and surface hardness measurements were performed as described above on three commercially available products.

| Cement cure time: | Dycal (L D Caulk) | 3 min |
|---|---|---|
| | Life regular (Kerr-Sybron | 9 min |
| | Life fast set (Kerr-Syrbon) | 3 min |
| Light cure time | Prisma VLC Dycal | 2 min |
| Surface hardness: | Dycal | 6.5 VHN |
| | Life regular | 10.5 VHN |
| | Life fast set | 10.0 VHN |

EXAMPLE 2

Triethanolamine salicylate was prepared by the method described in Example 1 for the preparation of glycerol salicylate except that the reactants were triethanolamine (32.9 g; 0.22 moles), methyl salicylate (67.1 g; 0.44 moles) and sodium methoxide (0.82 g; 0.015 moles). The final methyl salicylate level was 20.0%.

Methacrylated triethanolamine salicylate (MTS) was prepared by the method described in Example 1 for the preparation of methacrylated glycerol salicylate except that the reactants were triethanolamine salicylate (as above) (69 g), pyridine (32 g; 0.41 moles) dissolved in dry methylene chloride (140 ml). To this was added methacroyl chloride (40.6 g; 0.39 moles) in dry methylene chloride (84 ml). The product was worked up as described in Example 1.

Using the same catalyst system and method as in Example 1, the time to gellation was 212 seconds. The cement cure time of a mixture of equal amounts of the above MTS with 'Dycal' was 940 seconds; the surface hardness of cured material from that mixture as evaluated by the method in part C of Example 1 was 14.9 VHN.

EXAMPLE 3

Trimethylolethane salicylate was prepared by the method described in Example 1 for the preparation of glycerol salicylate except that the reactants were trimethylolethane (60.1 g; 0.5 moles), methyl salicylate (119.7 g; 0.788 moles), sodium methoxide (0.82 g; 0.015 moles). The final methyl salicylate level was 10.0%.

Methacrylated trimethylolethane salicylate (MES) was prepared by the method described in Example 1 for the preparation of methacrylated glycerol salicylate except that the reactants were triethanolamine salicylate (as above) (138 g), pyridine (58 g; 0.73 moles) dissolved in dry methylene chloride (250 ml). To this was added methacroyl chloride (72.4 g; 0.69 moles) in dry methylene chloride (150 ml). The product was worked up as described in Example 1.

Using the same catalyst system and method as in Example 1, the time to gellation was 75 seconds. The cement cure time of a mixture of equal amounts of the above MES with 'Dycal' was 405 seconds; the surface hardness of cured material from that mixture as evaluated by the method in part C of Example 1 was 19.0 VHN.

EXAMPLE 4

Pentaerythritol salicylate was prepared by the method described in Example 1 for the preparation of glycerol salicylate except that the reactants were pentaerythritol (34.04 g; 0.25 moles), methyl salicylate (86.72 g; 0.57 moles) and sodium methoxide (0.41 g; 0.0075 moles). The final methyl salicylate level was 12.5%.

Methacrylated pentaerythritol salicylate (MPS) was prepared by the method described in Example 1 for the preparation of methacrylated glycerol salicylate except that the reactants were triethanolamine salicylate (as above) (47 g), pyridine (22 g; 0.28 moles) dissolved in dry methylene chloride (95 ml). To this was added methacroyl chloride (26.15 g; 0.25 moles) in dry methylene chloride (90 ml). The product was worked up as described in Example 1.

Using the same catalyst system and method as in Example 1, the time to gellation was 270 seconds. The cement cure time of a mixture of equal amounts of the above MPS with 'Dycal' was 90 seconds; the surface hardness of cured material from that mixture as evaluated by the method in part C of Example 1 was 22.3 VHN.

EXAMPLE 5

A formulation suitable for clinical evaluation was prepared as follows:

|  | (g) |
| --- | --- |
| Component A |  |
| Methacrylated glycerol salicylate (Example 1) | 50 |
| Barium sulphate | 35 |
| "Aerosil" OX50 (Degussa) | 15 |
| Component B |  |
| Vinyl urethane resin (a) | 22.5 |
| Triethyleneglycol dimethacrylate | 22.5 |
| Calcium hydroxide | 25 |
| Barium sulphate | 25 |
| "Aerosil" OX50 | 5 |
| Camphorquinone | 0.38 |
| Dimethylaminoethylmethacrylate | 0.23 |

(a) as prepared in Example 1 European Patent 53442

Both components were prepared by mixing the constituents on a twin-roll mill until homogeneity was achieved.

For a laboratory evaluation, equal weights of the two components were mixed together by hand. The cement cure time was 210 seconds. At any time up to 3 minutes, the composition could be cured by visible light; the light cure time was 30 seconds, both cure times using the method described in Example 1.

Cured material had a flexural modulus of 5.52 GPa, a flexural strength of 49.8 MPa and a surface hardness of 20 VHN.

EXAMPLE 6

A sample of the mixture evaulated in Example 5 was also evaluated in the clinic.

It was found that immediately on mixing the two components, the mixture flowed into a tooth cavity because the viscosity was low. When placed as a liner, the mixture adhered rapidly to dentin even in slightly damp conditions, unlike conventional two-pack materials. After about 90 seconds, the viscosity was found to increase, this was found to be the most workable phase, during which excess material could be removed from enamel margins and the final shape could be established. After light-curing by radiation in the wavelength range 400 mµ to 500 mµ, the material became very hard, with adequate properties to be used under amalgam, gold or composite. Adhesion of the cured material was high and it was very difficult to remove excess cured cement. The two-stage viscosity is considered to be an advantage because low initial viscosity facilitates placement on a liner whilst the second higher viscosity enables build up of material for a base.

What we claim is:

1. A dental cement composition having a first component which comprises an ethylenically polymerisable compound which contains both a salicylate group and at least one acrylate, alkacrylate, acrylamide or alkacrylamide group (hereinafter referred to as an acrylosalicylate), and a second component which comprises a calcium hydroxide or a suitable precursor to calcium hydroxide, and a photosensitive catalyst the ingredients of which may be present in either or both of the first and second components.

2. A cement composition according to claim 1 in which the salicylate is an ester of salicylic acid and a polyhydric alcohol containing 2 to 8 hydroxy groups.

3. A cement composition according to claim 2 in which the polyhydric alcohol is a triol.

4. A cement composition according to claim 2 in which the molar ratio of units derived from salicylic acid to units derived from the polyhydric alcohol is 0.1:1 to m:1 where m is the number of hydroxyl groups in the polyhydric alcohol.

5. A cement composition according to claim 1 in which the ratio of (alk)acrylyl groups to salicylate groups in the acrylosalicylate is 0.3:1 to 3:1.

6. A cement composition according to claim 1 in which the alkacrylate is a methacrylate.

7. A cement composition according to claim 1 in which the cement contains an additional filler.

8. A method of producing a dental lining which comprises mixing the two components of the cement composition as claimed in claim 1, applying the mixture to a tooth, allowing the composition to cement-cure and curing the mixture by irradiation having wavelength in the range 400 m$\mu$ to 600 m$\mu$.

* * * * *